United States Patent [19]

Ojo-Amaize

[11] Patent Number: 5,747,270
[45] Date of Patent: May 5, 1998

[54] METHOD OF SCREENING FOR SILICONE-SPECIFIC HYPERSENSITIVITY

[75] Inventor: Emmanuel Ojo-Amaize, Glendora, Calif.

[73] Assignee: Specialty Laboratories, Inc., Santa Monica, Calif.

[21] Appl. No.: 418,637

[22] Filed: Apr. 6, 1995

Related U.S. Application Data

[63] Continuation-in-part of Ser. No. 245,975, May 18, 1994, abandoned.

[51] Int. Cl.$^6$ .................................................. G01N 33/567
[52] U.S. Cl. .................... 435/7.24; 435/2; 435/240.2; 436/503; 436/518; 436/72
[58] Field of Search ........................... 435/7.24, 240.2; 436/506, 508, 72, 503

[56] References Cited

PUBLICATIONS

Stites, 1980. "Clinical laboratory methods of detecting cellular immune function," in *Basic & Clinical Immunology* (H.H. fudenberg et al. eds.) Lange Medical Publications, Los Altos. pp. 382–387.

Gilboa et al. 1988. Metal allergy in cashiers. Acta Derm Venereol (Stockh) 68: 317–324.

Stejskal et al. 1990. Lymphocyte transformation test for diagnosis of isothiazolinone allergy in man. J. Invest Dermatol 94:798–802.

Stejskal et al. 1986. The lymphocyte transformation test for diagnosis of drug–induced occupational allergy. J. Allergy Clin Immunol 77:411–426.

Shelton et al. 1985. Delayed hypersensitivity reaction to silicone breast implants. Annals of Allergy 54: 361. Abstract #96.

Goldblum et al. 1992. Antibodies to silicone elastomers and reactions to ventriculoperitoneal shunts. Lancet 340: 510–513, and 800.

Kossovsky et al. 1992. Clinical reviews: mammary implants. J. Applied Biomaterials 3: 1–4.

Moseley et al., 1988. Divergent effects of silica on lymphocyte proliferation and immunoglobulin production. J. Appl. Physiol. 65: 350–357.

Ojo–Amaize et al., 1994. Silicone–specific blood lymphocyte response in women with silicone breast implants. Clinical and Diagnostic Laboratory Immunology 1: 689–695.

Van Voorhis et al., 1983. Relative efficacy of human monocytes and dendritic cells as accessory cells for T cell replication. J. Exp. Med. 158: 174–191.

*Primary Examiner*—Paula K. Hutzell
*Assistant Examiner*—James L. Grun
*Attorney, Agent, or Firm*—Harris F. Brotman

[57] ABSTRACT

An in vitro method for diagnosing hypersensitivity to silicon (e) antigen in subjects not previously exposed to silicon(e). The method involves obtaining a subset of lymphocytes from non-sensitized subjects and contacting the lymphocytes with silicon(e) for a sufficient period of time to cause sensitizing and proliferative responses.

4 Claims, 4 Drawing Sheets

METHOD OF SCREENING FOR SILICONE-SPECIFIC HYPERSENSITIVITY

BACKGROUND OF THE INVENTION

This application is a continuation-in-part of parent application Ser. No. 08/245,975, filed May 18, 1994 now abandoned.

1. Field of the Invention

This invention relates to a method for diagnosing immune reactions associated with silicone implants in subjects. In particular, this invention relates to specific screening blood tests demonstrating silicone-specific T cell responses in women at risk for silicone-induced disease exposed to silicone breast implants, and in women who have not been previously exposed to silicone.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

Approximately one to two million women in the United States have had silicone breast implants inserted for reconstruction or augmentation mammoplasty. Although originally regarded as inert in the human body, silicone has polymeric and hydrophobic characteristics, and its electrostatic charges and organic sidegroups make silicone a potential immunogen (32).

Silicone products may be associated with various complications which may involve an immune reaction to silicone (4, 16, 31) or, in some cases, a systemic autoimmune disease (26, 29, 19).

Although silicone is widely used in humans for various cosmetic/prosthetic purposes, the understanding of the immunological effects of silicone is rudimentary. Silicone is known to induce inflammatory responses (8, 5), lymphadenopathy and giant-cell granulomas (25, 27). Despite these reports, confusion exists over which medical complications have a cause-and-effect relationship and which represent coincidental findings (26).

Workers in this field have difficulty or are unable to distinguish between non-specific local reactions and reactions that have an immunological basis. It is not known how various immunological mechanisms, such as cell mediated responses and humoral antibody responses, are involved in the development of clinical complications associated with silicone gel implants. A specific cellular response to silicone has never been demonstrated by standard immunological assays, nor is there any test which can predict or indicate any specific immune response to silicone, which is what a test must do to prove adverse health effects. Accordingly, further developments are needed to elucidate the immunological mechanisms underlying clinical complications associated with silicone gel implants, and diagnostic methods to accurately identify silicone-specific immunological autoreactions underlying or causing such complications.

SUMMARY OF THE INVENTION

In accordance with the present invention, a method is provided for diagnosing silicone-specific T-cell proliferative response in patients at risk for silicone-specific immune response. The method has the advantage of being more highly predictive of medical complications of silicone gel implants than other methods described to date. The method overcomes the above-mentioned problems and provides a defined method of diagnosing a woman who has silicone-related disease, or a woman who is non-symptomatic but has a hyper-reactive or hypersensitive state to silicone, a prerequisite for symptomatic expression of silicone-related disease. Accordingly, the method of the invention has the advantage of identifying a specific immune response to silicone.

The method of the invention comprises the step of obtaining a sample of lymphocytes from a subject at risk for silicone-specific immune-response leading to silicone-specific disease. The lymphocytes are contacted with silicon or a derivative thereof for a period of time sufficient to indicate a proliferative response of the lymphocytes. The proliferative response is quantitated and compared to the proliferative response of lymphocytes obtained from subjects who are not at risk for such immune response.

The invention further provides a method for identifying hypersensitivity or hyperactivity to silicon(e) antigens in non-sensitized subjects, i.e. those who have not been previously exposed to silica or silicone products. The in vitro method comprises the step of contacting lymphocytes from a non-sensitized subject with silicon antigen or a derivative thereof for a period of time sufficient to sensitize the lymphocytes and indicate a proliferative response. A subsequent step quantitates the proliferative response, thereby identifying hypersensitive subjects.

The above discussed and many other features and attendant advantages of the present invention will become better understood by reference to the following detailed description of the invention when taken in conjunction with the accompanying drawings.

DETAILED DESCRIPTION OF THE INVENTION

Definitions

Figure 1:
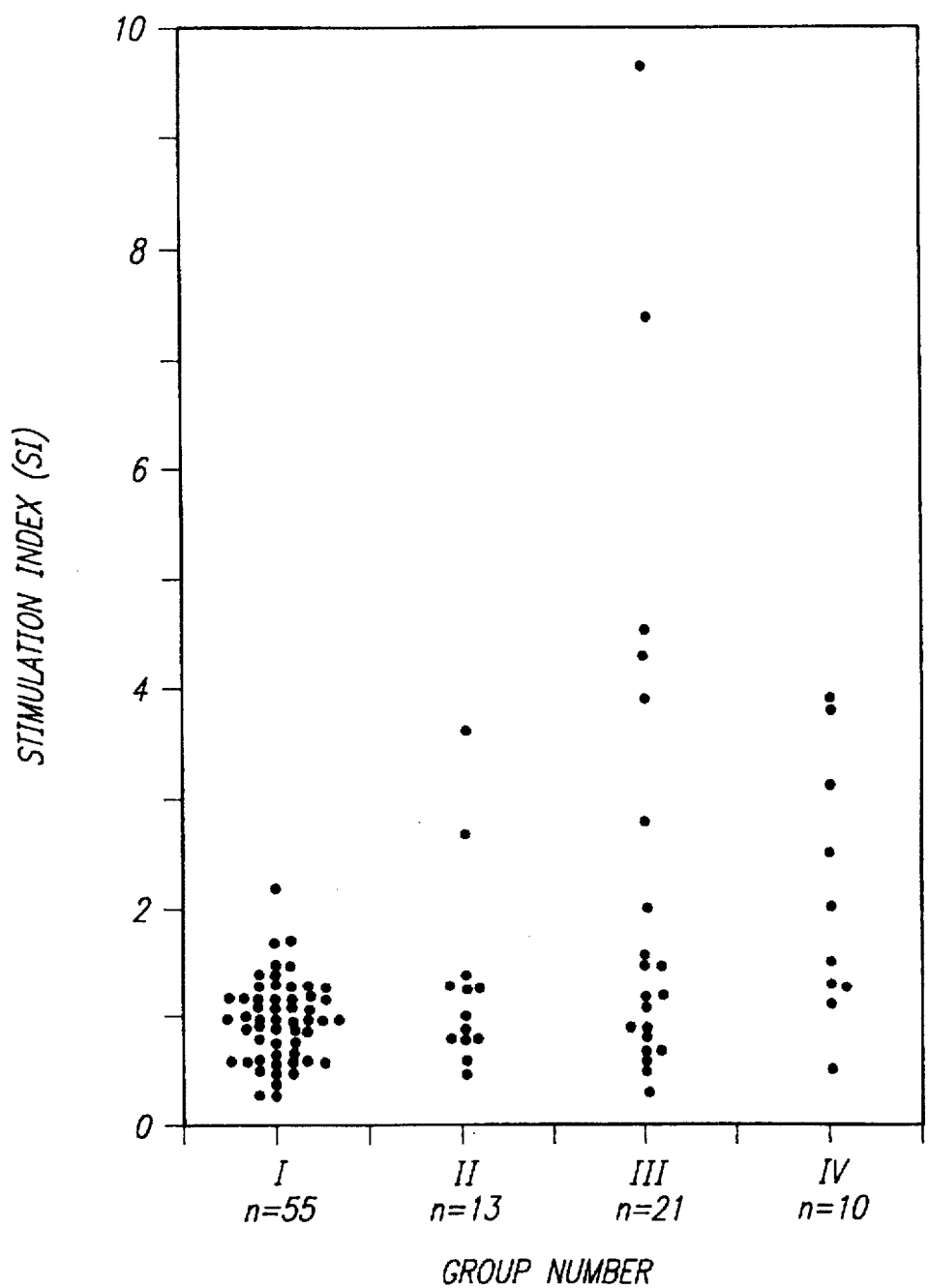
FIG. 1 shows silicone-specific T-cell response profile of women with silicone gel breast implants.

As used herein, the term "sensitized" refers to subjects who have been exposed to silica or silicone products, and whose lymphocytes have undergone a primary immune response to silicon(e) antigen. "Non-sensitized" refers to subjects who have not been previously exposed to silica or silicone products, and whose lymphocytes have not undergone a primary immune response to silicon(e) antigen. "Hypersensitive" refers to subjects who are predisposed or at high risk for developing hypersensitivity reaction (4, 16, 19, 26, 29, 31) (i.e. hyperactivity) to silicon(e) antigens after undergoing silicone gel implantation.

As used herein, "at risk" refers to subjects who (1) have been exposed to an immunogenic bolus of silicon(e) due to implant surgery; or (2) are subject to surgery involving silicone gel implant or any foreign material containing silicone, such as sutures, drug delivery devices, or other implantable devices (e.g. breast, penile, facial reconstruction or augmentation). Among such "at risk" subjects are those who may have a genotype as a factor rendering them hypersensitive or hyperactive to immunostimulation by exposure to a bolus of silicon(e) antigen.

Certain advantages are provided by the method of the present invention for diagnosing silicone-specific immune response in the blood of subjects who are at risk for silicone-specific immune response, in particular, subjects with silicone breast implants or those in whom such implants have been explanted. These advantages include positive identification of abnormal immune reactions associated with silicone. The method of the invention provides a specific screening blood test which correlates with symptoms in women with implanted or explanted silicone breast prostheses.

The invention further provides an in vitro immunization method which offers the advantage of identifying non-sensitized subjects (i.e. those who have not been exposed to silica or silicone products) who are hypersensitive to silicone antigens.

General Methods

This invention relies on routine techniques in the field of immunochemistry. A basic text disclosing the general methods of use in this invention is *Manual of Clinical Laboratory Immunology*, 3rd Edition, N. R. Rose et al., eds. (1986).

The invention provides a method for diagnosing silicone-specific T-cell proliferative response in subjects at risk for silicone-specific immune response, namely, subjects with implanted or explanted silicone-gel prostheses.

Silicone refers to a group of silicon-containing compounds which include fluids, gels, rubbers, sponges, foams and resins (1). Silicone in various forms is incorporated into silicone gel implant prostheses for a variety of procedures (34).

The steps of the method involve obtaining a sample of lymphocytes from a sensitized subject who is at risk, contacting the lymphocytes with silicone for a sufficient period of time to cause a proliferative response of the lymphocytes, quantitating the proliferative response, and comparing the proliferative response of the lymphocytes to the proliferative response of lymphocytes obtained from non-symptomatic subjects who are not at risk for silicone-specific immune response, that is, those who have not had silicone gel implants.

Typically, a symptomatic subject is chronically fatigued and has symptoms such as fibromyalgia, insomnia, skin disorders, lung problems, headaches, joint pain, muscle cramps, arthritis, allergies, and anemia (5, 8, 11, 16, 19, 25–29, 31, 32).

The step of obtaining lymphocytes from sensitized subjects who are either symptomatic or at risk preferably involves drawing peripheral blood by venipuncture. Other sources of lymphocytes which may be used in the method of the invention are surgically obtained samples of spleen or lymph node, bronchoalveolar lavage.

Methods for isolating peripheral blood mononuclear cells (PBMC) from blood are well known in the art (3), as are methods for obtaining lymphocytes from samples of spleen or lymph node, or from bronchoalveolar lavage (23, 33).

The method of the invention for obtaining a sample of lymphocytes involves selecting a subset of T-lymphocytes, in particular the $CD4^+$ helper/inducer subset of $CD3^+$ cells. Methods for obtaining particular subsets of lymphocytes are commercially available (Applied Immune Sciences, Santa Clara, Calif.). Any of the conventional methods for obtaining T-lymphocyte subsets may be used. An exemplary method, which is described in the Example below, involves a cell culture flask system to negatively select either $CD4^+$ or $CD8^+$ cells using immobilized monoclonal antibodies as ligands for specifically binding to surface antigens of targeted cells.

Antigen solutions of silicone were prepared as described below in the Example. Silicone gel was obtained from Mentor Corporation, Santa Barbara, Calif. The silicone antigen, in the form of a solution of either $SiO_2$, elemental silicon, or silicone gel, was used in the method of the invention to contact the obtained lymphocytes ($CD4^+$ helper/inducer subset of $CD3^+$ cells). The antigen contacted the lymphocytes for a sufficient period of time to cause a proliferative response. Although the method of the invention prefers periods of contact between silicone antigen and the lymphocytes of either 5 days or 7 days, other time periods are useful in the method of the invention, those time periods being from about one day to about ten days.

As used in the present specification, "proliferative response" refers to activated cells, and indicates primed cells that have been activated by a given antigen and can produce more cells that have been so activated, and mediate the reactions of cell mediated immunity (36).

Various labels are useful for quantitating proliferative response. The label used is not particularly critical. Any of the well known labels may be used, including a radionucleotide, an enzyme, a fluorescent agent, and a chromophore (35). As described below in the Example, four to 16 hours before the end of the period of contact between the silicone antigen and the obtained lymphocytes, a $^3H$ thymidine label was added to the microtiter wells in which the obtained lymphocytes and silicone antigen were cultured. The amount of radioactive label incorporated into the proliferating cells was quantitated by harvesting the cells onto glass filters which were placed in a scintillation counter. A stimulation index was calculated as described below in the Example and presented in Tables 3 and 4. The stimulation index is compared to the stimulation index quantitated from silicone-antigen exposed $CD4^+$ helper/inducer subset of $CD3^+$ cells obtained from healthy women without breast implants. Comparing the proliferative response of the lymphocytes obtained from symptomatic women to the proliferative response of lymphocytes obtained from healthy women, i.e. non-symptomatic women without silicone gel implants accordingly permits the achievement of the method of the invention to diagnose silicone specific T-cell proliferative response in symptomatic subjects. J. Immunol. Meth. 1991; 142:199-206.

The following Examples are offered by way of illustration and is not intended to limit the invention in any manner.

EXAMPLES

Reagents and Equipment

The following reagents and equipment were employed in this Example. Lithium sulfate ($Li_2SO_4$), nickel sulfate hexhydrate ($NiSO_4 \cdot 6H_2O$), zirconyl chloride hydrate ($ZrOCl_2$), mercuric chloride ($HgCl_2$), chromic trioxide ($CrO_3$), magnesium sulfate ($MgSO_4$), silicon dioxide ($SiO_2$) were purchased from Sigma Chemical Company (St. Louis, Mo.). Other reagents and sources included beryllium sulfate tetrahydrate ($BeSO_4 \cdot 4H_2O$) (Aldrich Chemical Co. Inc., Milwaukee, Wis.), elemental silicon (Si) and silicone gel (Mentor Corporation, Santa Barbara, Calif.) RPMI-1640 medium and Hanks' balanced salt solution (HBSS) (Irvine, N.J.), Penicillin/Streptomycin mixture (Gibco Laboratories, Grand Island, N.Y.) and pooled human AB serum was obtained from Gemini Bioproducts, Inc. (Calabasas, Calif.). Fluorescence-activated sell sorter lysing buffer, phycoerythrin (PE)-labeled monoclonal antibody (Mab) Leu2a (CD8), and fluorescein isotheiocyanate (FITC)-labeled MAB Leu3a (CD4) purchased from (Becton dickinson, San Jose, Calif.). An AIS MicroCellector for the selection of T cell subsets was obtained from Applied Immune Sciences, Inc. (Menlo Park, Calif.). Quantikine human IL-4 enzyme immunoassay (EIA) kit was purchased from Research and Diagnostic Systems (Minneapolis, Minn.) and Intertest-2x EIA kit for human IL-2 detection from Genzyme Corporation (Cambridge, Mass.).

Blood Donors

Peripheral blood was obtained by venipuncture from subjects who were not at risk for silicone-specific immune response, 55 healthy women who did not have breast implants (Group I).

Subjects at risk included 13 women with breast implants who reported feeling well and pleased with their silicone gel implants formed Group II. Group III consisted of 21 women with breast implants who had various symptoms including fatigue, fibromyalgia and autoimmune disease. Group IV comprised 10 women who had their breast implants removed due to overt connective tissue diseases. The fibromyalgia diagnoses were made by rheumatologists using criteria of the American College of Rheumatology (5). Each woman provided detailed information regarding date of placement of all implants, indications for implantation, type(s) of implants, reported overt leakage or rupture, the duration of symptoms and the types and severity of their symptoms.

Measurement of Blood Serum Silicone Levels

Serum samples were analyzed using an inductively coupled plasma atomic emission spectrometer (ICP-AES) (Applied Research Laboratories, Dearborn, Mich.). The samples were introduced to the argon plasma by using a peristaltic pump (Gilson Medical Electronics, Inc., Middleton, Wis.) and auto sampler (Gilson). Detailed methodology and instruction were given to subjects 12 hours before serum samples were collected, as described in (20, 9, 10).

Preparation of Lymphocytes

Peripheral blood mononuclear cells (PBMC) were isolated from heparinized venous blood by Ficoll-Hypaque gradient centrifugation (3), washed three times with HBSS. The cells' viability was determined by the trypan blue dye exclusion method (15, 18). Cells were resuspended in complete culture medium (20% heat-inactivated pooled human AB serum, 2 mM L-glutamine, 2 mM N-2-hydroxyethylpiperazine-N'-2-ethanesulfonic acid (HEPES) and 1% Penicillin-Streptomycin (10,000 units/ml)) to $2\times10^6$ cells/ml.

Selection of T-Lymphocyte Subsets

The AIS MicroCellector Cell Culture Flask System was used to negatively select either $CD4^+$ or $CD8^+$ cells accordingly to manufacturer's instructions. In the MicroCellector Cell Culture Flask System monoclonal antibodies (MAbs) are permanently bound to the surface. When blood cells are added, the immobilized ligands bind to surface antigens of the targeted cells. Cells not bearing the recognized antigens remain free in suspension. A quantity of $4\times10^7$ PBMC cells was added to AIS CD4 T-25 (Mab Leu3a-bound, for depletion of $CD4^+$ cells and selection for $CD8^+$ cells) or CD8 T-25 flask (MAb Leu3a-bound, for depletion of $CD8^+$ cells and selection for $CD4^+$ cells). After incubation for one hour at room temperature (RT) on a flat non-vibrating surface, non-adherent cells were removed, washed twice in complete medium, counted and analyzed by flow cytometry.

Flow Cytometric Analysis of T-Lymphocyte Subsets

Following lysis of any remaining erythrocytes, PBMC were stained with a mixture of MAbs, CD8PE and CD4FITC. Stained cells were analyzed on a FACScan cytometer (Beckton Dickinson). Lymphocytes were gaited by forward and right angle light scattering.

Antigens $SiO_2$ was prepared in $H_2O$ and dissolved with a small volume of concentrated $H_2SO_4$. A 2 mM stock solution was prepared and stored at RT until used for assay at final concentrations of 10 µM, 1 µM, and 0.1 µM in complete culture medium.

A stock solution of elemental silicon was prepared by dissolving silicon in $H_2O$ at a concentration of 1 mg/ml. It was stored at RT until used for assay at final concentrations of 10 µg/ml, 1 µg/ml and 0.1 µ/ml in complete culture medium.

A stock solution of 1 gram of silicone gel dissolved in hexane to yield 100 mg/ml was stored at RT until used for assay at final concentrations of 10 micrograms/ml, 1 µg/ml and 0.1 µg/ml in complete culture medium.

Lymphoproliferation (Proliferative Response)

Lymphocytes ($2\times10^5/0.1$ ml complete culture medium) were dispensed in quadruplicate into 96-well round-bottomed microtiter plates and antigen in complete culture medium were added (0.1 ml/well). Non-stimulated control wells contained 0.1 ml of cells and 0.1 ml of complete culture medium. Cultures were maintained in a humid incubator at 370° C. in an atmosphere of 5% $CO_2$ for optimal time points (5 and 7 days, respectively). Four to 16 hours before harvesting, the cultures in each well were pulsed with 1 microCi tritiated thymidine (specific activity 719.5 mCi/mg, Dupont, Wilmington, Del.). Cells harvested onto glass filters (Packard, Downers Grove, Ill.) with a 96-well automatic cell harvester (TOMTEC, Hamden, Conn.) were counted directly on a Matrix 9600 direct beta counter (Packard, Downers Grove, Ill.). Data were expressed as the stimulation index (SI) plus/minus standard error (SE) of the means (counts per minute, CPM) for stimulated well/CPM of unstimulated control cultures).

Determination of Dose-Response Curve for Secondary Response to Stimulation with $SiO_2$, Silicon, or Silicone Gel Viable cells, adjusted to $2\times10^6$/ml were dispensed in 0.1 ml volumes ($2\times10^5$ cells/well) into microtiter wells and challenged with different concentrations of $SiO_2$, silicon or silicone gel in 0.1 ml volumes, respectively. The cultures were incubated for 5 or 7 days. Four to 16 hours before the end of the culture period, the cultures were pulsed with 1 microCi of $^3$H thymidine. Blastogenic responses were determined as described above.

Determination of Kinetics of Secondary Response

Viable cells, adjusted to $2\times10^6$/ml were dispensed in 0.1 ml volumes ($2\times10^5$ cells/well) into microtiter wells and challenged with different concentrations of $SiO_2$, silicon or silicone gel in 0.1 ml volumes, respectively. The cultures were incubated for various periods of time (1, 3, 5, 7 and 9 days). Four to 16 hours before the end of the culture period, the cultures were pulsed with 1 microCi of $^3$H thymidine. Proliferative responses were determined as described above.

Evaluation of the Antigen Specificity of Silicone-Reactive Cells

The antigen specificity of silicone-reactive cells was evaluated by testing a battery of related metal salt antigens compared with silicon, $SiO_2$ and silicone gel. The following salts were tested at three different final concentrations (0.1, 1, and 10 µM): $BeSO_4$, $CrO_3$, $Li_2SO_4$, NiSO4, $ZrOCl_2$, $HgCl_2$, or $MgSO_4$. The level of blastogenic response after five or seven days of culture was measured as described above.

Establishment of SI Cutoff Values for Determination of Abnormal Response to either $SiO_2$, Silicone or Silicone Gel An abnormal or positive response is defined as a peak SI of more than 2.8 for $SiO_2$; greater than 2.1 for silicon or greater than 2.4 for silicone gel. These values are based on the blood mean peak SI plus 3 standard deviations of 40 healthy women ($SiO_2$); 15 healthy women (silicon) and 15 healthy women (silicone gel).

Determination of Cytokine Levels in Serum and Culture Supernatants

Levels of interleukin-2 and interleukin 4 in serum and culture supernatants were determined by enzyme-linked immunosorbent assay (EIA) as described by the manufacturers (Quantikine R and D Systems, Minneapolis, Minn.). Levels of IFN-gamma were also determined by a commercially available EIA kit (Gibco, BRL, Grand Island, N.Y.).

Statistical Analysis

All values are mean plus/minus standard errors of the means. Statistical comparisons were made with the Student's t-test.

RESULTS

Characterization of women with silicone breast implants. The 99 women who voluntarily participated in the study were divided into 4 groups at the completion of the study as the study was blinded. Group I consisted of 55 healthy women without breast implants. Group II was 10 healthy women with breast implants. Group III consisted of 21 women with breast implants who had chronic fatigue and musculo-skeletal symptoms and Group IV was 10 women who had their prostheses explanted but still presented with clinical symptoms similar to the women in Group III (Table 1).

TABLE 1

Characterization of 41 Women With Silicone Gel Breast Implants

| | | | Type of Implant | | | |
|---|---|---|---|---|---|---|
| Group | Clinical Characteristic | No. of Subjects | Silicone-gel | Lumen[a] | Meme[b] | Unknown |
| I | No implants, healthy | 55 | — | — | — | — |
| II | Implants, well, asymptomatic | 13 | 8 | 3 | 1 | 1 |
| III | Implants, asymptomatic-chronic fatigue, musculo-skeletal symptoms, autoimmune disease | 21 | 13 | 3 | 1 | 4 |
| IV | Explants, symptomatic-chronic fatigue, muscoskeletal symptoms, autoimmune disease | 10 | 7 | 3 | 0 | 0 |

[a]Lumen type is silicone inside and saline outside
[b]Meme type is polyurethane foam coated Establishment of normal reference range for assessment of cellular response to stimulation with three forms of silicone. Of the 55 healthy women without implants used to establish the normal reference range, 40 were used for $SiO_2$, and 15 were used for silicon and silicone gel, respectively. the mean SI+3 SD are shown for each of 3 concentrations and for each antigen (Table 2). Average of all 3 SD values at all concentrations for each antigen are shown and used as the cutoff value for that antigen.

TABLE 2

Establishment of Normal Reference Range for Determination of Degree of Stimulation With Three Forms of Silicone In Healthy Women Without Breast Implants

| | | Mean SI + SD | | | Average of 3SD | Established |
|---|---|---|---|---|---|---|
| Type of Silicone | # of subjects per group | 0.1 µM | 1.0 µM | 10 µM | values at all concentrations | SI Cutoff Value |
| $SiO_2$ | 40 | 2.4 | 2.9 | 3.1 | 2.8 | 2.8 |
| Silicon* | 15 | 2.9 | 2.0 | 1.4 | 2.1 | 2.1 |
| Silicone-gel* | 15 | 3.0 | 1.8 | 2.3 | 2.4 | 2.4 |

*Elemental silicon and silicone-gel were used in microgram concentrations (0.1 µg, 1.0 µg and 10 µ/mL) on cells of the same 15 healthy women.

Silicone-specific T cell proliferation response in women with silicone gel breast implants. Abnormal silicone-specific T cell proliferative responses were observed in 0% of Group I, 15.3 of Group II, 28.6% of Group III and 30% of Group IV (Table 3). The responses were significantly higher in both Groups III and IV as compared to Group I (p <0.01). SI's of each individual woman in each group are shown in FIG. 1, which shows the highest response (SI) obtained for each woman in each Group at any of the three concentrations tested against any of the forms of silicon or silicone derivatives tested. Group I represents healthy, not at risk controls; Group II represents asymptomatic, at risk women with breast implants; Group III represents symptomatic women with breast implants, and Group IV consists of symptomatic women who have explanted their silicone breast prostheses.

TABLE 3

Silicone-Specific T Cell Proliferation Response in Women with Silicone Gel Breast Implants

| Group[a] | Subjects | No. of Serum Silicone-Positive Individuals per group | No. of Individuals per Group with Abnormal T Cell Response to Silicone | % of Total |
|---|---|---|---|---|
| I | 55 | 0/55 | 0/55 | 0 |
| II | 12 | 5/12 | 2/13 | 15.3 |
| III | 21 | 0/21 | 6/21 | 28.6 |
| IV | 10 | 0/10 | 3/10 | 30.0 |

[a]The groups are characterized in Table 1.
[b]Individuals with SI values greater than the cutoff values shown in Table 1 ($SiO_2$ = 2.8; Silicone gel = 2.4) at any concentration, at any of the two optimal time points (5- or 7-day culture) and to any of the three forms of silicon.

Figure 2:
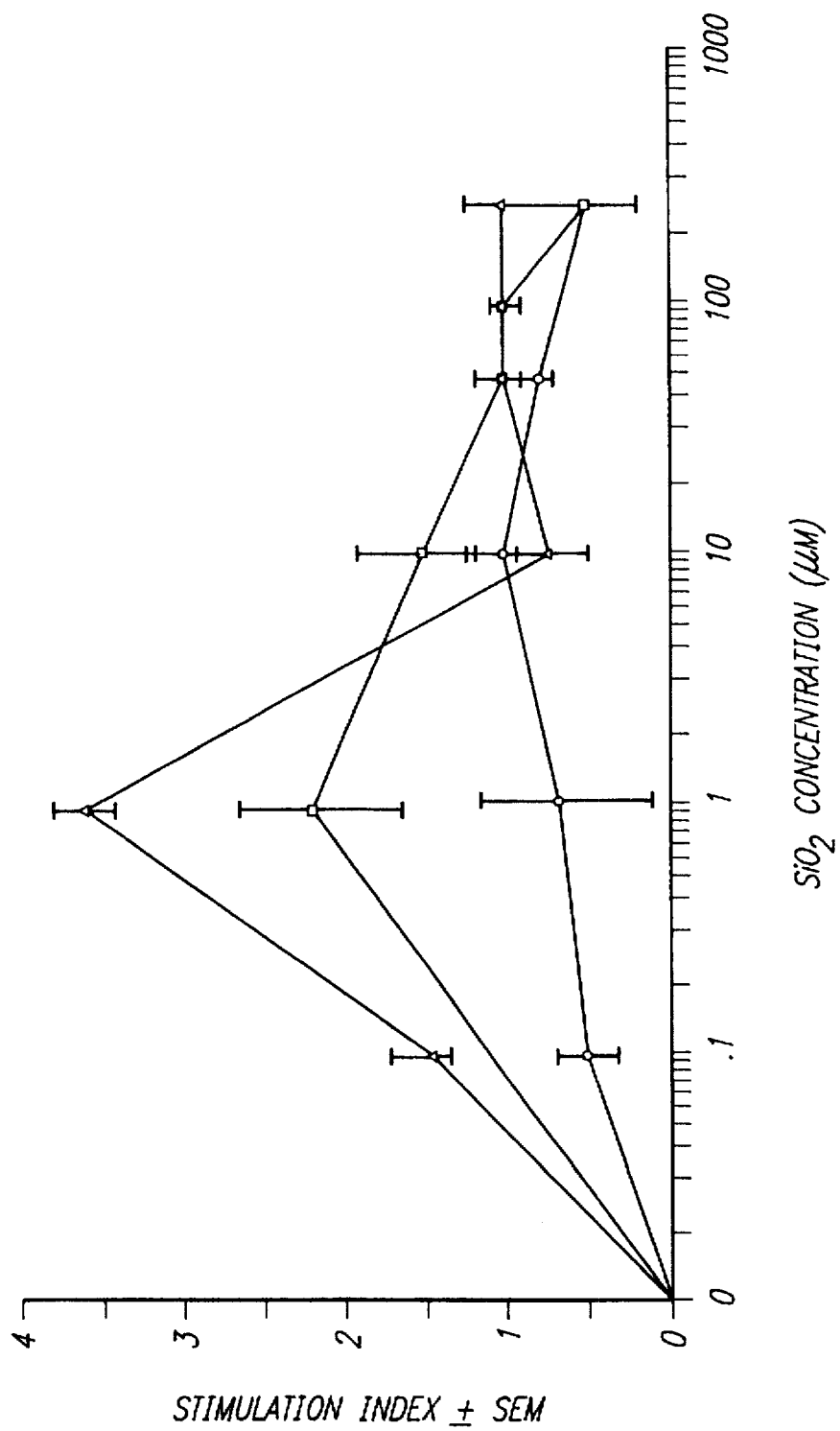
FIG. 2 shows the dose-dependent proliferative response of PBMC from women with silicone breast implants to stimulation with $SiO_2$.

Dose-dependent proliferative response of PBMC from women with silicone breast implants to stimulate with $SiO_2$. PBMC from 3 women previously shown to be reactive or non-reactive were used to establish the dose response curve. One of these women had an abnormal response to $SiO_2$ and the other two had responses below the cutoff value for $SiO_2$. $SiO_2$ concentrations of 0.1, 1.0 and 10 μM induced higher levels of responses than concentrations >50 μM, as shown in FIG. 2. In FIG. 2, triangles represent a woman with abnormal cellular response to $SiO_2$, squares represent a woman with normal (intermediate) response to $SiO_2$, and circles represent a woman with normal (low) response to $SiO_2$. Similarly, concentrations of 0.1, 1.0 and 10 μ/mL for silicon and silicone gel induced optimal levels of responses. Therefore, an individual was considered sensitized to silicone if the individual responds positively to either $SiO_2$, silicon or silicone gel at any of the three concentrations (FIG. 2).

Kinetics of proliferative response of PBMC from a woman with silicone breast implants to stimulation with $SiO_2$, silicon or silicone gel. PBMC from a woman who had previously been determined to have abnormal SI to stimulation with $SiO_2$ and to silicone gel were used for the kinetics experiment. Following stimulation with 0.1, 1.0 or 10 μM $SiO_2$, or 0.1, 1.0 or 10 μg/mL silicon or silicone gel, respectively, cells were cultured for varying periods of time (1–9 days). All forms of silicone induced maximal responses between days 5 and 7 (FIG. 3) with day 7 being the best.

Figure 3:
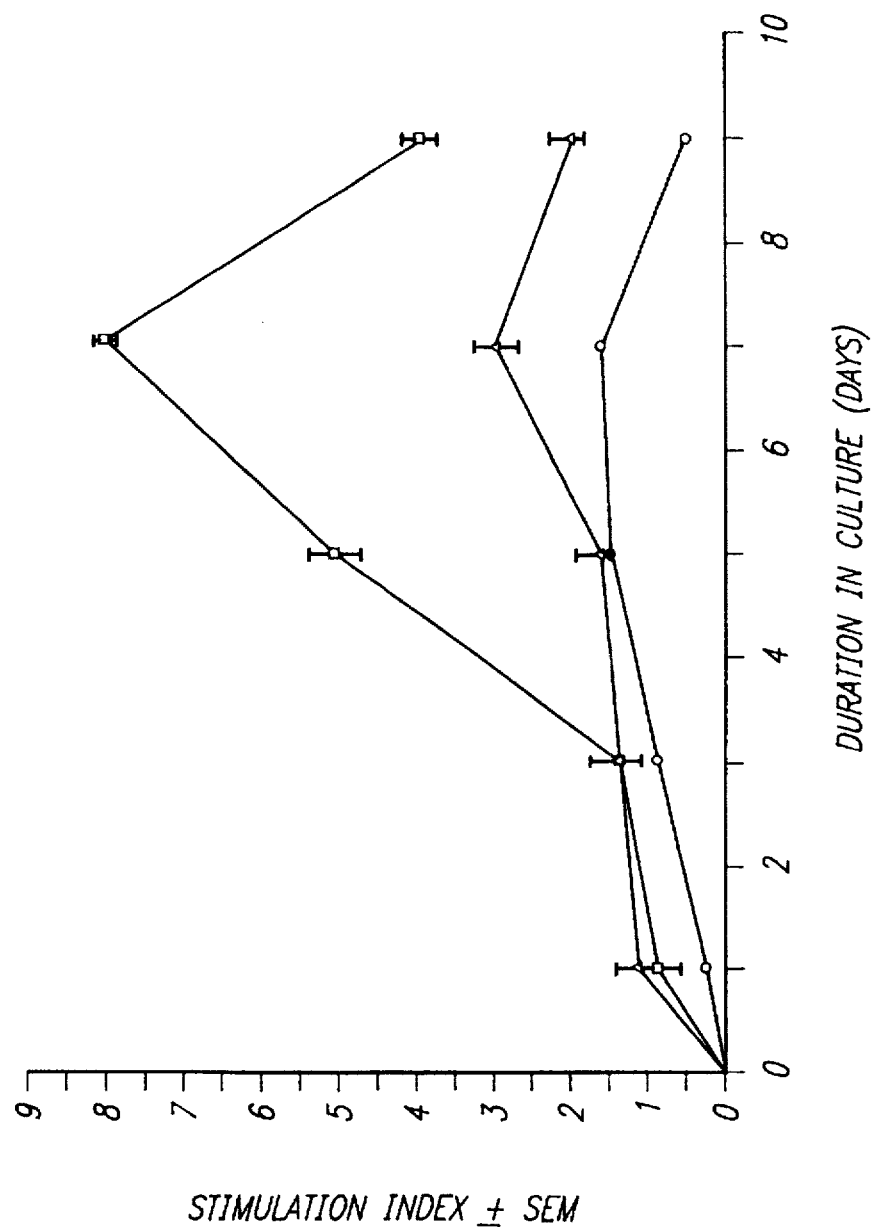
FIG. 3 shows the kinetics of secondary; proliferative response of PBMC from a woman with silicone breast implant to stimulation with $SiO_2$, silicon or silicone gel.

In FIG. 3, the squares represent PBMC from a woman with silicone breast implant who had an abnormal cellular response to $SiO_2$; the triangles represent the response to silicone gel; and the circles are a normal response to silicon. The results are peak SIs at any one of the following $SiO_2$ concentrations: 0.1, 1.0 or 10 micromolar.

These results are similar to beryllium-induced T cell response (15); either of two optimal time points is appropriate for determining the response to beryllium. An individual with S1 values greater than the cutoff values for each of the antigens, at any of the three concentrations and at any of the two optimal time points (5- or 7-day culture) was regarded as having an abnormal T cell proliferative response to silicone.

Specificity of the silicone-reactive PBMC. PBMC from a symptomatic woman with silicone breast implant who was previously shown to have abnormal response to stimulation with $SiO_2$, was used to demonstrate that specific immune response could be generated against $SiO_2$. All the antigen metals tested (except $SiO_2$ and silicone gel) failed to induce significant secondary responses in the silicone-sensitized woman (FIG. 4).

Figure 4:
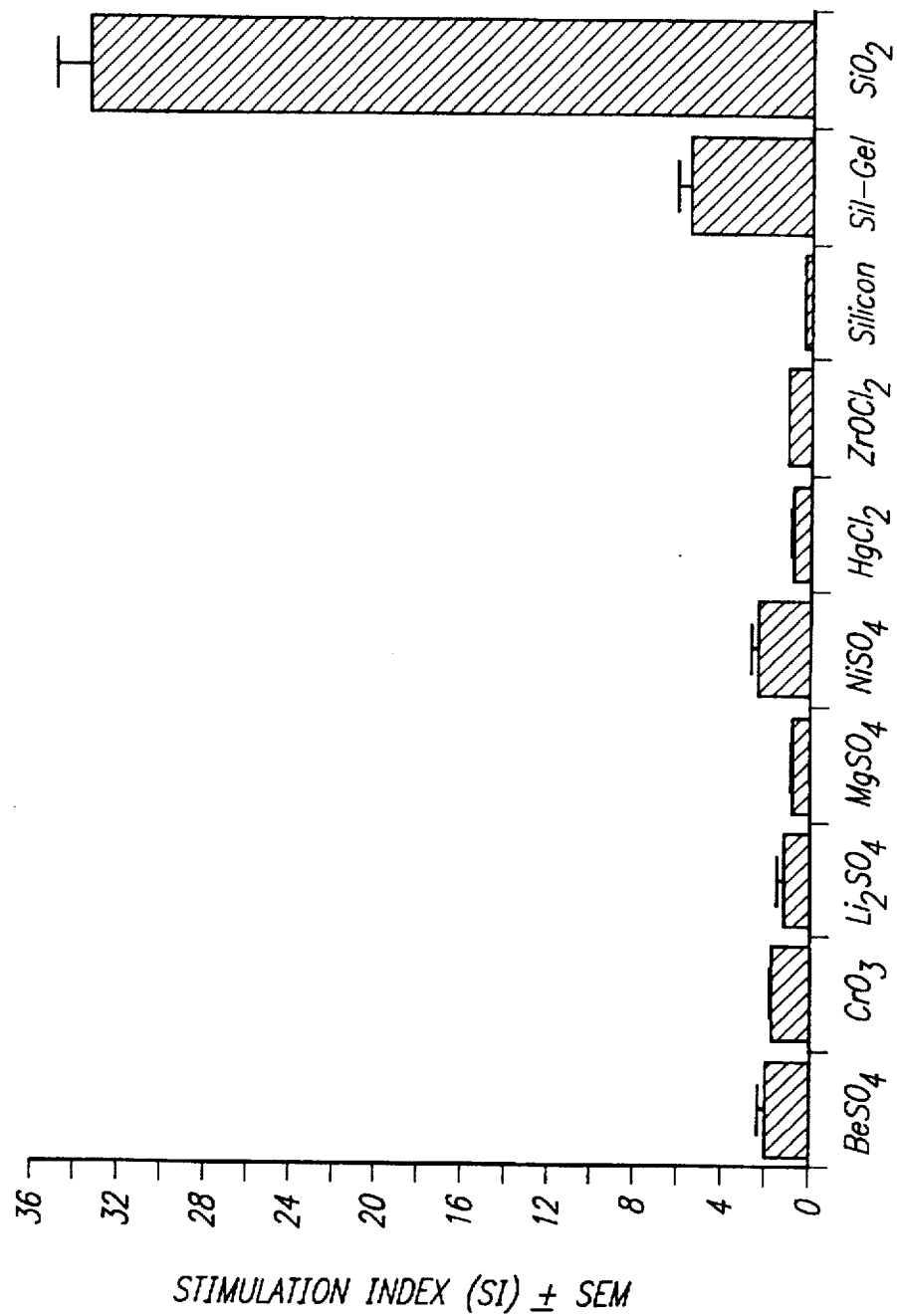
FIG. 4 shows the specificity of the secondary response to silicone.

The results shown in FIG. 4 are peak SIs at any one of the three concentrations (0.1, 1.0, 10 micromolar) any one of the two time points (5- or 7-day culture).

Although the particular woman used for this experiment did not respond to elemental silicon, some of the women in Groups III and IV responded to elemental silicon (Table 4).

TABLE 4

Responsiveness of 11 Women With Abnormal Response to Different Forms of Silicon

| Subject Number | STIMULATION INDEX (SI)[a] | | | | | | | | | Group Number[b] |
|---|---|---|---|---|---|---|---|---|---|---|
| | $SiO_2$ (μM) | | | Silicon (μg/mL) | | | Silicone-gel (μg/mL) | | | |
| | 0.1 | 1.0 | 10.0 | 0.1 | 1.0 | 10.0 | 0.1 | 1.0 | 10.0 | |
| 1. | | | | | 2.7 | | | | | II |
| 2. | | | | | 3.6 | | | | | |
| 3. | | 4.3 | | 3.1 | 2.9 | | | | | |
| 4. | | 9.6 | 7.7 | | | | | | 4.8 | III |
| 5. | | | | | 2.2 | | | | | |
| 6. | | | | | | | | 4.5 | | |
| 7. | | | | | | | | | 2.8 | |
| 8. | | 7.4 | | 4.3 | | | | | | |
| 9. | 3.1 | | | | | | | | | IV |
| | | | | | | 2.4 | | | | |
| 10. | 3.9 | | | | 3.8 | | | | | |
| 11. | | | | | | | | | | |

[a]The highest SI values obtained for each subject in either 5- or 7-day culture.
[b]The groups are characterized in Table 1.

Effect of T cell subset depletion. After depletion with the AIS MicroCellector Cell Culture Flask, two-color immunofluorescence and flow cytometry demonstrated that the silicone-reactive cells possess the $CD4^+$ phenotype. No activity was found in the $CD8^{30}$ population of T cells (Table 5).

TABLE 5

Characterization of Silicone-Specific Lymphocytes According to Phenotype

| T-Cell Population | % of Cells Expressing T-Cell Subset Phenotype[a] | | Level of Silicone-Specific T-Cell Proliferative Response (SI)[b] |
|---|---|---|---|
| | CD4 | CD8 | |
| CD4 depleted | 8.8 | 91.2 | 0.9 ± 0.2 |
| CD8 depleted | 96.3 | 3.7 | 4.0 ± 0.6 |

[a]Values are percentages of cells expressing the designated antigens following depletion with the AIS MicroCellector Cell Culture Flash System and subjection to flow cytometric analysis.
[b]Each cell population was stimulated with 1.0 μg silicone gel for 7 days or left unstimulated. SI = CPM of stimulated cells/cpm of unstimulated cells. Cells were obtained from one of the 6 women in Group III with abnormal T cell proliferative response to silicone gel.

Cytokine profile of silicone-specific $CD4^+$ helper T cells. PBMC or purified $CD4^+$ T cells form non-sensitized healthy women failed to produce IL-2 or IL-4 upon stimulation with $SiO_2$. In contrast, PBMC or purified $CD4^+$ T cells from symptmatic women with silicone breast implants produced significant amounts of IL-2 but not IL-4 (Table 5). Surprisingly, the supernatants were negative for interferon γ.

The method of the present invention, accordingly is based on these findings which indicate that silicone acts as a specific sensitizing antigen in vivo, leading to a silicon-specific secondary immune response in vitro as measured by $^3$H-thymidine uptake of T cells responding to stimulation with either $SiO_2$, silicon or silicone gel.

Women with silicone breast implants are known to have several types of autoantibodies against different self antigens (32, 31, 29). The present findings show the involvement of CD4+ T helper and T inducer cells in silicone-induced immune reactions and suggest that at least one of the mechanisms by which certain individuals with silicone prostheses produce autoantibodies is via the amplification of T cell help for autoreactive B-cells. The finding that more symptomatic implant-exposed women developed silicone-specific T cell proliferative responses (compared with asymptomatic implant women, (Table 3)), supports the mechanism that autoimmune reactions prevalent among this group of women may be linked to loss of T cell regulation of autoreactivity of B cells. The fact that some individuals responded to all three forms of silicone whereas others responded only to one, two or none of the silicone forms, may reflect either differences in the level of in vivo priming, type of implant, genetic susceptibility, active immunosuppression or tolerance. The results demonstrating that there was no correlation between level of silicone-specific cellular response and blood serum silicone levels (Table 3) was consistent with antigen-specific amnestic response in the absence of circulating antigen.

In contrast to the small number (1.7%) of symptomatic women with silicone breast implants identified to be silicone antibody-positive by the silicone antibody test (14), the present invention identified 25% of such women to be silicone hyperactive by the T cell assay (Table 3).

TABLE 6

Cytokine Profile of Silicone-Specific CD4+ Helper T Cells

| Subject[a] | Group[b] | Type of Treatment in In Vitro | Cytokine Production | |
|---|---|---|---|---|
| | | | IL-2 (<5 Units) | IL-4 (<90 pg/mL) |
| 1 | I | PBMC or purified CD4+ T-cells cultured either in complete medium alone or with 2 µM SiO2 for 6 days | 0 | 0 |
| 2 | III | PBMC + 2 µM SiO$_2$ cultured in complete media for 6 days | 14.0 | 0 |
| 3 | IV | Purified CD4+ T cells cultured in complete media alone for 6 days | 12.6 | 0 |

[a]Cells were obtained from one woman in each of the representative Groups (I, III and IV, respectively). Each of the women from Groups III and IV had an abnormal T cell proliferative response to elemental silicone, SiO2 or silicone gel.
[b]The groups are characterized in Table 2.

The method of the present invention provides the advantage of being a silicon e-specific T ell proliferation test, unlike a silicone-specific antibody test. The present invention is less cumbersome to perform, is more specific and sensitive and permits the gathering of information on an individuals cellular abnormal reaction to either elemental silicon, SiO$_2$ or silicone gel.

Silicone-Specific T-Cell Proliferative Response in Women with Silicone Breast Implants: Correlation with Disease Severity.

In this study, proliferative responses of peripheral blood mononuclear cells from 167 women were measured by [$^3$H] thymidine uptake after exposure to SiO$_2$ Na$_2$ SiO$_3$, silicone gel or the T-cell mitogen phytohemagglutinin (PHA). The levels of proliferative responses are expressed as stimulation indices (SIs), obtained by dividing the counts per minute of stimulated cells by the counts per minute of unstimulated cells. Abnormal responses to SiO$_2$, Na$_2$ SiO$_3$ or silicone gel were defined as a SI of >3.0 (3 standard deviations above controls). Normal responses to PHA were defined as a SI of >50.

Of the 167 women tested, 79 had silicone breast implants, and 88 were healthy age-matched volunteer control women without breast implants. 41% (32/79) of the women with silicone breast implants showed T-cell reactivity versus 0% (0/88) of the controls. All the women (with or without implants) had normal responses (SI>50) to PHA. All 79 of the women with silicone implants were evaluated clinically. Seven of 79 (9%) had no symptoms. Of the remaining 72 symptomatic women, 7/72 (10%) had typical connective tissue disease, 72/72 (100%) had atypical connective tissue disease, 64/72 (88%) had atypical neurological disease and 65/72 (90%) had atypical skin disease. They were ranked for severity of disease on a disability rating scale of 0, 20, 35 and 100 percent disabled. Group I consisted of 88 healthy women without implants, group II consisted of 7 women with breast implants who felt healthy (0% disabled), group III consisted of 25 women with breast implants (20% disabled, group IV consisted of 36 women with breast implants (35% disabled) and group V consisted of 11 women with breast implants (100% disabled). None of the women in group I without implants had a positive silicone-specific T-cell reaction. In contrast, abnormal responses were observed in 14% (1/7) of group II, 40% (10/25) of group III, 39% (14/36) of group IV and 63% (7/11) of group V. These results demonstrate that abnormal silicone-specific T-cell responses exist in a significantly higher number of symptomatic versus asymptomatic women with silicone breast implants and suggest that cell-mediated immunity plays a role in the development and progression of autoimmune diseases associated with silicone.

In Vitro Immunization System to Identify Subjects at Risk for Development of Hypersensitive Reaction The purpose of this example was to identify hypersensitivity to silicon(e) antigens in lymphocytes taken from non-sensitized subjects as a means for identifying non-sensitized subjects at high risk for developing systemic autoimmune disease (36) after undergoing silicone gel implantation.

As used herein, non-sensitized subjects are subjects who have never been exposed to silica or silicone products, typically those individuals who have not undergone silicone gel implantation. Sensitized subjects are those whom have undergone silicone gel implantation.

Generation of sensitized cells in vitro.

Primary cultures of Na$_2$SiO$_3$, SiO$_2$ or silicone-contacted cells were initiated with 100, 10, and 1 µ/ml final concentration of each of the antigens, respectively. 2–3×10$^7$ viable peripheral blood mononuclear cells (PBMC) were seeded in complete RPMI-164-O culture medium (10% AB serum+ 1% penicillin-streptomycin 10,000 U/ml) at a concentration of 2×10$^6$ cells per ml in 25 cm$^2$ culture flasks with 0.2 µ-pore-size vented filter caps. Flasks were incubated on their flat sides at 37° in 5% CO$_2$ for 7–10 days.

Challenge of in vitro sensitized cells with either the sensitizing antigens or unrelated metal salt antigens Following contact with silicon(e) antigens to create sensitized non-adherent cells, the cultured cells were recovered from flasks, washed three times in Hanks-Balanced Salt Solution (HBSS) and resuspended in complete medium. Viable cells, adjusted to 2×10⁶/ml were dispensed in quadruplicate in 0.1 ml volumes (2×10⁵ cells per well) into U-bottom microtiter wells and challenged, i.e. further contacted with different concentrations (10, 1, and 0.1 µg/ml) of silicon(e) antigens or unrelated metal salts (BeSO$_4$, CrO$_3$, Li$_2$SO$_4$, MgSO$_4$, NiSO$_4$, HgCl$_2$, ZrOCl$_2$) also in 0.1 ml volumes. Nonstimulated control wells contained 0.1 ml of cells and 0.1 ml of complete medium. Cultures were maintained in a humid incubator at 37° in an atmosphere of 5% CO$_2$ for 5 days. Four to 16 hours before harvesting, the cultures in each well were pulsed with 1 µCi of tritiated thymidine (specific activity, 719.5 mCi/mg; Dupont, Wilmington, Del.). Cells were harvested onto glass fiber filters (Packard, Downers Grove, Ill.) with a 96-well automatic cell harvester (TOMTEC, Hamden, Conn.) and counted directly on a Matrix 9600 direct beta counter (Packard). Data were expressed as the stimulation index (SI) (counts per minute for stimulated wells/counts per minute for unstimulated control cultures =/− standard error of the mean.

Establishment of SI Cutoff Value for Determination of Level of Responsiveness A positive response was defined as a peak stimulation index (SI) of [>=3.0]. This value was based on the blood mean peak SI plus 3 standard deviations previously established for in vitro sensitization to silicon(e) antigens (37).

Screening of 20 Non-Sensitized, Healthy Subjects

Using the silicon(e)-antigen specific in vitro immunization system achieved by contacting lymphocytes taken from non-sensitized subjects, the inventor screened twenty healthy women volunteers between the ages of 20 and 45. None of the volunteers had prior exposure to silica or silicone products. All were screened for silicon(e) antigen hypersensitivity with the in vitro immunization system.

Variation Among Different Women in the Capacity to be Sensitized to Silicon(e) Antigen In Vitro The results shown in Table 7 below demonstrate that there are differences among the subjects in the capacity to be sensitized to silicon(e) antigens in vitro. Based on the level of individual responsiveness to secondary stimulation with silicon(e) antigens, the subjects were divided into a responder group and a non-responder group. As shown in Table 7, two of 20 subjects tested were classified into the responder group. Eighteen of 20 subjects tested were classified into the non-responder group.

TABLE 7

Grouping of 20 healthy women without silicone breast implants according to level of responsiveness to immunization with silica, silicate, or silicone

| Level of Responsiveness | SI Range | Average SI (± SD) of Invidiuals per Group | No. of Positive Individuals per Group/Total | % of Total |
|---|---|---|---|---|
| Responder | ≧3.0 | 4.3 ± 1.1 | 2/20 | 10 |
| Non-Responder | <3.0 | 1.4 ± 0.6 | 18/20 | 90 |

Using the claimed method, the present method embodies an in vitro immunization system which identifies non-sensitized subjects who are hypersensitive to silicon(e) antigens. In the method of the invention, silicone or a derivative thereof in contact with non-sensitized lymphocytes for a sufficient period of time acted as (i) a specific inducer of a primary response, i.e. sensitizing agent in vitro, and (ii) as an inducer of a silicon(e) specific secondary immune response in vitro as measured by ³H- thymidine uptake of T cells responding to stimulation with either SiO$_2$, silicate, silicon, or silicone gel. The method identified hypersensitive subjects.

Hypersensitive subjects are those who are predisposed or at high risk for developing hypersensitivity reaction (4, 16, 19, 26, 29, 31) to silicon(e) antigens after undergoing silicone gel implantation. The finding herein of variation in a population of non-sensitized women to in vitro silicon(e)-antigen induced sensitization and proliferation pointed to underlying genetic and/or environmental factors which may predispose certain subjects to silicon(e)-antigen hypersensitivity in vivo.

As presented above, silicon(e)-specific T-cells were detected in the blood of women with silicone gel breast implants. The claimed method involves an in vitro system to immunize "naive", i.e. non-sensitized non-immune PBMCs from healthy women without prior exposure to silica or silicone. The claimed method achieved the objective of identifying healthy subjects never exposed to silicon or silicone products who are either responders or non-responders, subjects who vary in their capacity to mount a silicon(e)-specific T-cell response. Responders, accordingly, are subjects identified by the claimed method who are hypersensitive or hyperactive upon in vivo exposure to silicon(e) antigen following silicone gel implantation.

It is an object of the present invention to use the results of the claimed method as a basis for counseling subjects who are contemplating silicone gel implantation for augmentation or reconstruction mammoplasty, or other procedures involving silicone gel implantation.

Having thus disclosed exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

References

1. Ballantyne, D. L., T. D. Rees, and I. Seidman. 1965. Silicone fluid: response to massive subcutaneous injections of dimethylpolysiloxane fluid in animals. Plast. Reconstr. Surg. 36:330-338

2. Bargon, J., H. Kronenberger, L. Bergman, et al. 1986. Lymphocyte transformation test in a group of foundry workers exposed to beryllium and non-exposed controls. Eur. J. Respir. Dis. 69 (Suppl. 136):211-215.

3. Boyum, A. 1968. Separation of leukocytes from blood and bone marrow. Scand. J. Clin. Lab. Invest. 21 (Suppl. 97):77-89.

4. Breedveld, F. C. and D. E. Trentham. 1987. Progress in the understanding of inducible models of chronic arthritis. Rheum. Dis. Clin. North Am. 13:531-544.

5. Claman, H. H., and A. D. Robertson. 1994. Antinuclear antibodies and breast implants. WJM 160:225-228.

6. Clarke, S. M. 1991. A novel enzyme-linked immunosorbent assay (ELISA) for the detection of beryllium antibodies. J. Immunol. Meth. 137:65-72.

7. Digby, J. M. 1982. Malignant lymphoma with intranodal silicone rubber particles following metacarpophalangeal joint replacements. The Hand 14:326-328.

8. Endo, L. P., N. L. Edwards, S. Longley, et al. 1987. Silicone and rheumatic diseases. Semin. Arthritis Rheum. 17:112-118.

9. Gitelman, H. J., and F. R. Alderman, and S. J. Perry. 1992. Silicon accumulation in dialysis patients. Am. J. Kidney Dis. 19:140-143.

10. Gitelman, H. J., and F. R. Alderman. 1990. Determination of Silicon in Biological Samples Using Electrothermal Atomic Absorption Spectrometry. J. Analyt. Atomic Spectrometry 5:687-689.

11. Gordon, M., and P. G. Bullough. 1982. Synovial and osseous inflammation in failed silicone rubber prosthesis: a report of six cases. J. Bone Joint Surg. 64A:574-580.

12. Jones, W. W., and W. R. Williams. 1983. Value of beryllium lymphocyte transformation tests in chronic beryllium disease and in potentially exposed workers. Thorax 38:41-44.

13. Kapsenberg, M. L., E. A. Wierenga, F. E. M. Stiedema, A. M. B. C. Tiggelman and J. D. Bos. 1992. TH1 lymphokine production profiles of nickel-specific CD4 T-lymphocyte clones from nickel contact allergic and non-allergic individuals. J. Invest. Dermatol. 98:59-63.

14. Kossovsky, N., M. Zeidler, G. Chun, et al. 1993. Surface dependent antigens identified by high binding avidity of serum antibodies in a subpopulation of patients with breast prostheses. J. Appl. Biomaterials 4:281-288.

15. Kreiss, K., L. S. Newman, M. M. Mroz, and P. A. Campbell. 1989; Screening blood test identifies subclinical beryllium disease. J. Occup. Med. 31:603-608.

16. Miyoshi, K. T., T. Miyramura, Y. Kobayashi, et al. 1964. hypergammaglobulinemia by prolonged adjunvanticity in man. Disorders developed after augmentation mammoplasty. Jpn. J. Med. 2122:9-14.

17. Ojo-Amaize, E. A., M. S. Agopian, and J. B. Peter. 1994. Novel in vitro method for identification of individuals at risk for beryllium hypersensitivity. Clin. Diagn. Lab. Immunol. 1:164-171.

18. Ojo-Amaize, E. A., M. S. Agopian, T. N. Markham, and J. B. Peter. 1992. Primary sensitization and restimulation of human lymphocytes with beryllium in vitro. J. Allergy Clin. Immunol. 89:203 (Abstract).

19. Press, R. I., C. L. Peebles, Y. Kumagai, R. L. Ochs, and E. M. Tan. 1992. Antinuclear autoantibodies in women with silicone breast implants. Lancet 340:1304-1307.

20. Roberts, N. B. and P. Williams. 1990. Silicon measurement in serum and urine by direct current plasma emission spectrometry. Clin. Chem. 36:1460-1465.

21. Rogers, L. A., J. A. Longtime; M. B. Garnick, et al. 1988. Silicone lymphadenopathy in a long distance runner: complication of a silastic prosthesis. Hum. Pathol. 19:1237-1239.

22. Romagnoli, P., G. A. Spinas, and F. Sinigaglia. 1992. Gold-specific T cells in Rheumatoid arthritis patients treated with gold. J. Clin. Invest. 89:254-258.

23. Rossman, M., J. Kern, J. Elias, et al. 1988. Proliferative response of bronchoalveloar lymphocytes to beryllium: a test for chronic beryllium disease. Ann. Intern. Med. 108:687-693.

24. Saltini, C., K. Winestock, M. Kirby, P. Pinkston, and R. G. Crystal. 1989. Maintenance of alveolitis in patients with chronic beryllium disease by beryllium - specific helper T cells. N. Engl. J. Med. 320:1103-1109.

25. Sergott, T. J., J. P. Limoli, C. M. Baldwin, and D. R. Laub. 1986. Human adjuvant disease, possible autoimmune disease after silicone implantation: a review of the literature, case studies and speculation for the future. Plastic Reconstr. Surg. 78:104-114.

26. Shons, A. R., and W. Schubert. 1992. Silicone breast implants and immune disease. Ann. Plast. Surg. 28:491-501.

27. Spierra, H. 1988. Scleroderma after silicone augmentation mammoplasty. JAMA 260:236-238.

28. Stokes, R. F., and M. D. Rossman. 1991. Blood cells proliferation response to beryllium: analysis by receiver-operating characteristics. J. Occup. Med. 33:23-28.

29. Varga, J., R. Chumacher, and S. A. Jimenez. 1989. Systemic sclerosis after augmentation mammoplasty with silicone implants. Ann. Intern. Med. 111:377-383.

30. Winchurch, R. A. 1988. Activation of thymocyte responses to interleukin-1 by zinc. Clin. Immunol. Immunopathol. 47:174-180.

31. Yoshida, K. 1913. Post mammoplasty disorder as an adjuvant disease of men. Shikoku Acta. Med. 29:318-332.

32. Yoshida, S. H., C. C. Chang, S. S. Teber and M. E. Gershwin. 1993. Silicon and silicone: theoretical and clinical implications of breast implants. Regul. Toxicol. Pharmacol. 17:3-18.

33. Cutts, J. H. 1970. Cell separation methods in hematology. Academic Press, London.

34. Arkles, B., and P. Redinger. 1983. Silicones in biomedical applications. In Biocompatible Plymers, Metals and Composites (M. Szychez, Ed.) pp. 749-768. Technomic Publishing, Lancaster, Pa.

35. Blaheta, R. A., et al. (1991) A Rapid Non-Radioactive Fluorescence Assay for the Measurement of Both Cell Number and Proliferation. J. Immunol. Meth. 142:199-206.

36. W. J. Herbert, P. C. Wilkinson (eds) A Dictionary of Immunology, (1977), 2nd ed.

37. Yoshida, S. H., Teuber, S. S., German, J. B., and Gershwin, M. E. (1994), Immunotoxicity of silicone: Implications of oxidant balance towards adjuvant activity, Fd Chem Toxic 32(1):1089-1100.

38. Ojo-Amaize, E. A., Conte, V., Lin, H-C, Brucker, r. F., Agopian, M. S., and Peter, J. B. (1994), Silicone-specific blood lymphocyte response in women with silicone breast implants, Clin. Diagn. Lab Immunol. 1(6):689-695.

What is claimed is:

1. A method of screening for potential hypersensitivity to a silicone polymer antigen in a non-sensitized subject who has not received a silicone gel implant, comprising the steps of:

(a) obtaining a sample of lymphocytes from said non-sensitized subject;

(b) contacting said lymphocytes with silicone polymer antigen for a period of time sufficient to produce sensitized lymphocytes;

(c) recovering said sensitized lymphocytes;

(d) further contacting said sensitized lymphocytes with said silicone polymer antigen for a period of time sufficient to indicate a proliferative response of said sensitized lymphocytes; and (e) quantitating said proliferative response wherein an elevated response is comparison to controls is indicative of potential hypersensitivity to said silicone polymer antigen in said non-sensitized subject.

2. The method of claim 1 wherein said period of time is from about one day to about fifteen days.

3. The method of claim 1 wherein said lymphocytes are T cells.

4. The method of claim 3 wherein said T cells are a CD4$^+$ helper/inducer subset of CD3$^+$ cells.

* * * * *

UNITED STATES PATENT AND TRADEMARK OFFICE
CERTIFICATE OF CORRECTION

PATENT NO. : 5,747,270
DATED : May 5, 1998
INVENTOR(S) : Emmanuel A Ojo-Amaize

It is certified that error appears in the above-indentified patent and that said Letters Patent is hereby corrected as shown below:

Col. 16, line 56
  replace "is (first occurrence)"
  with --in--.

Signed and Sealed this

Seventh Day of July, 1998

Attest:

BRUCE LEHMAN

Attesting Officer    Commissioner of Patents and Trademarks